(12) United States Patent  (10) Patent No.: US 9,499,709 B2
Carlini et al.  (45) Date of Patent: Nov. 22, 2016

(54) OLIGOMERIC ROSIN ESTERS FOR USE IN INKS

(71) Applicant: Xerox Corporation, Norwalk, CT (US)

(72) Inventors: Rina Carlini, Oakville (CA); Adela Goredema, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 277 days.

(21) Appl. No.: 13/680,237

(22) Filed: Nov. 19, 2012

(65) Prior Publication Data

US 2014/0142334 A1  May 22, 2014

(51) Int. Cl.
  *C07C 69/74*  (2006.01)
  *C09D 11/34*  (2014.01)
  *C07C 69/753*  (2006.01)

(52) U.S. Cl.
  CPC ............ *C09D 11/34* (2013.01); *C07C 69/753* (2013.01); *C07C 2101/14* (2013.01); *C07C 2103/54* (2013.01); *C07C 2103/86* (2013.01)

(58) Field of Classification Search
  None
  See application file for complete search history.

(56) References Cited

U.S. PATENT DOCUMENTS 2,517,563 A * 8/1950 Harris .......................... 562/404
4,265,782 A * 5/1981 Armstrong et al. .......... 510/467

OTHER PUBLICATIONS

Bardyshev, I.I., "Diterpenoid Carboxylic Acid Anhydrides of the Abietane, Pimarane, and Isopimarane Series," Russian Journal of Organic Chemistry, vol. 35, No. 1, 1999, pp. 41-55.

(Continued)

*Primary Examiner* — Karl J Puttlitz

(74) *Attorney, Agent, or Firm* — MDIP LLC

(57) ABSTRACT

Disclosed are ester compounds of the formulae

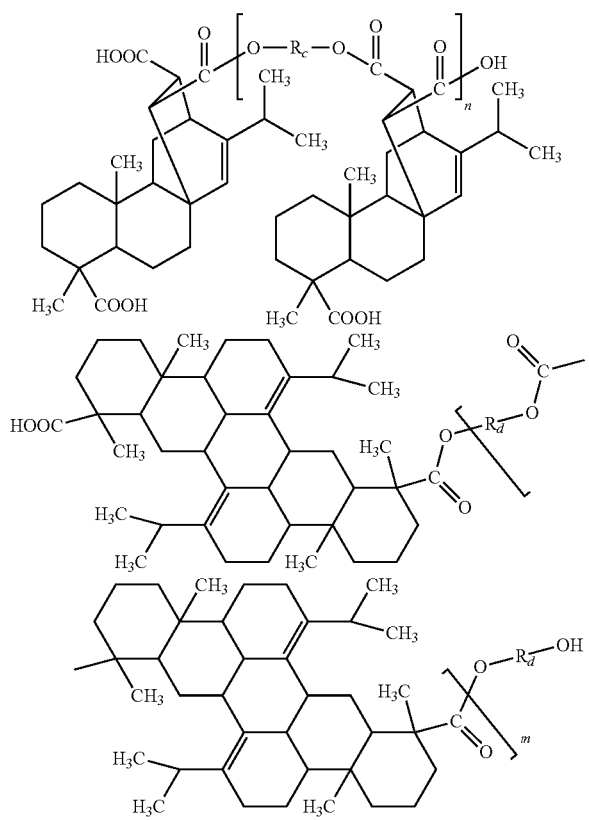

wherein $R_c$ is alkylene, arylene, arylalkylene, or alkylarylene as further defined herein, $R_d$ is alkylene, arylene, arylalkylene, or alkylarylene as further defined herein, and m and n are integers representing the numbers of repeat monomer units. The materials are suitable for use in inks and other applications.

13 Claims, 1 Drawing Sheet

(56) References Cited

OTHER PUBLICATIONS

Belelie et al., U.S. Appl. No. 13/095,636, filed Apr. 27, 2011, entitled "Solid Ink Compositions Comprising Crystalline-Amorphous Mixtures".
Carlini et al., U.S. Appl. No. 13/196,157, filed Aug. 2, 2011, entitled "Phase Change Inks Containing Oxazoline Compounds and Polyterpene Resins".
Goredema et al., U.S. Appl. No. 13/196,227, filed Aug. 2, 2011, entitled "Phase Change Inks Containing Crystalline Trans-Cinnamic Diesters and Amorphous Isosorbide Oligomers."
Morimitsu et al., U.S. Appl. No. 13/095,715, filed Apr. 27, 2011, entitled "Solid Ink Compositions Comprising Crystalline Esters of Tartaric Acid".
Farrugia et al., U.S. Appl. No. 12/714,677, filed Mar. 1, 2010, entitled "Bio-Based Amorphous Polyester Resins for Emulsion Aggregation Toners".
Sacripante et al., U.S. Appl. No. 13/007,683, filed Jan. 17, 2011, entitled "Rosin-Based Resin and Toner Containing Same".
Farrugia et al., U.S. Appl. No. 13/108,166, filed May 16, 2011, entitled "Rosin-Based Resin and Toner Containing Same".
Zhou et al., U.S. Appl. No. 13/326,242, filed Dec. 14, 2011, entitled "Toners With Improved Dielectric Loss".
Carlini et al., U.S. (Not Yet Assigned), filed concurrently herewith, entitled "Phase Change Inks Containing Oligomeric Rosin Esters". Nov. 19, 2012.
Goredema et al., U.S. (Not Yet Assigned), filed concurrently herewith, entitled "Ester Resin Compositions". Nov. 19, 2012.
Goredema et al., U.S. (Not Yet Assigned), filed concurrently herewith, entitled "Ink Compositions Incorporating Ester Resins". Nov. 19, 2012.
Goredema et al., U.S. (Not Yet Assigned), filed concurrently herewith, entitled "Bio-renewable Fast Crystallizing Phase Change Inks". Nov. 19, 2012.
Van Besien et al., U.S. (Not Yet Assigned), filed concurrently herewith, entitled "Bio-Renewable Phase Change Inks Comprising Recycled Resin Materials". Nov. 19, 2012.
H. P. Kaufmann et al., "Isomeric naphthoic sulfimides, a contribution to the theory of dulcigenic groups," Berichte der Deutschen Chemischen Gesellschaft [Abteilung] B: Abhandlungen, vol. 55B, pp. 1499-1508. (Abstract) Nov. 19, 2012.

\* cited by examiner

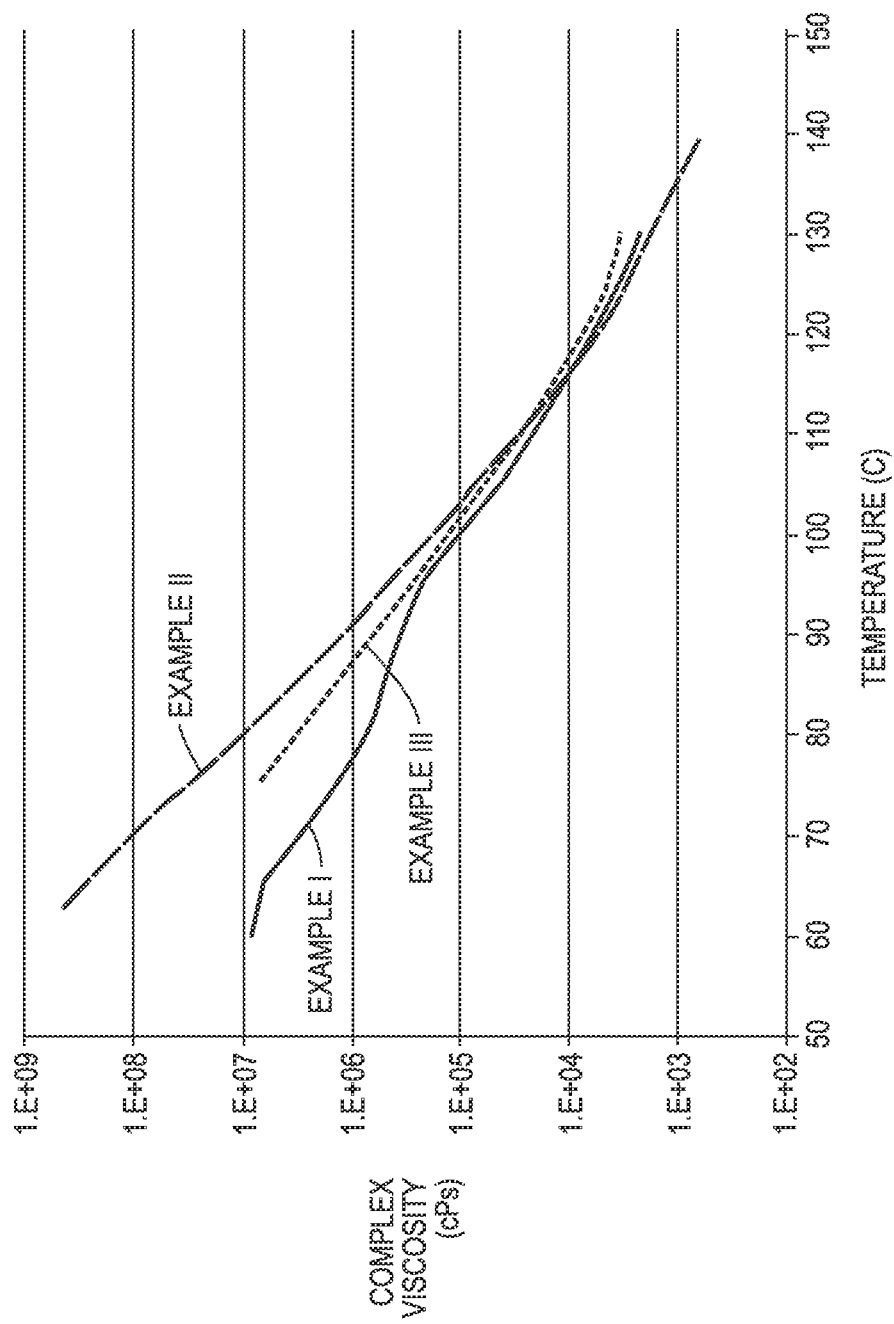

OLIGOMERIC ROSIN ESTERS FOR USE IN INKS

CROSS-REFERENCE TO RELATED APPLICATIONS

Reference is made to U.S. application Ser. No. 13/095, 636, filed Apr. 27, 2011, entitled "Solid Ink Compositions Comprising Crystalline-Amorphous Mixtures," with the named inventors Jennifer L. Belelie, Peter G. Odell, Stephan V. Drappel, Kentaro Morimitsu, Naveen Chopra, Marcel P. Breton, Gabriel Iftime, C. Geoffrey Allen, and Rina Carlini, the disclosure of which is totally incorporated herein by reference.

Reference is made to U.S. application Ser. No. 13/196, 157, filed Aug. 2, 2011, entitled "Phase Change Inks Containing Oxazoline Compounds and Polyterpene Resins," with the named inventors Rina Carlini, Adela Goredema, Guerino G. Sacripante, Caroline M. Turek, and Edward G. Zwartz, the disclosure of which is totally incorporated herein by reference.

Reference is made to U.S. application Ser. No. 13/196, 227, filed Aug. 2, 2011, entitled "Phase Change Inks Containing Crystalline Trans-Cinnamic Diesters and Amorphous Isosorbide Oligomers," with the named inventors Adela Goredema, Rina Carlini, Caroline M. Turek, Guerino G. Sacripante, and Edward G. Zwartz, the disclosure of which is totally incorporated herein by reference.

Reference is made to U.S. application Ser. No. 13/095, 715, filed Apr. 27, 2011, entitled "Solid Ink Compositions Comprising Crystalline Esters of Tartaric Acid," with the named inventors Kentaro Morimitsu, Jennifer L. Belelie, Naveen Chopra, Stephan V. Drappel, Corey Tracy, and Peter G. Odell, the disclosure of which is totally incorporated herein by reference.

Reference is made to U.S. application Ser. No. 12/714, 677, filed Mar. 1, 2010, entitled "Bio-Based Amorphous Polyester Resins for Emulsion Aggregation Toners," with the named inventors Valerie M. Farrugia, Guerino G. Sacripante, Ke Zhou, Edward G. Zwartz, and Michael S. Hawkins, the disclosure of which is totally incorporated herein by reference.

Reference is made to U.S. application Ser. No. 13/007, 683, filed Jan. 17, 2011, entitled "Rosin-Based Resin and Toner Containing Same," with the named inventors Guerino G. Sacripante, Ke Zhou, Edward G. Zwartz, Paul J. Gerroir, and Michael S. Hawkins, the disclosure of which is totally incorporated herein by reference.

Reference is made to U.S. application Ser. No. 13/108, 166, filed May 16, 2011, entitled "Rosin-Based Resin and Toner Containing Same," with the named inventors Valerie M. Farrugia, Ke Zhou, Guerino G. Sacripante, Rina Carlini, and Paul J. Gerroir, the disclosure of which is totally incorporated herein by reference.

Reference is made to U.S. application Ser. No. 13/326, 242, filed Dec. 14, 2011, entitled "Toners With Improved Dielectric Loss," with the named inventors Ke Zhou, Rina Carlini, Daryl W. Vanbesien, Cuong Vong, Karen A. Moffat, and Richard P. N. Veregin, the disclosure of which is totally incorporated herein by reference.

Reference is made to U.S. Pub. No. 20140137767 entitled "Phase Change Inks Containing Oligomeric Rosin Esters," with the named inventors Rina Carlini, Adela Goredema, Edward G. Zwartz, Kentaro Morimitsu, and Gail Song, the disclosure of which is totally incorporated herein by reference.

Reference is made to U.S. Pub. No. 20140142335 entitled "Ester Resin Compositions," with the named inventors Adela Goredema, Rina Carlini, Jennifer L. Belelie, Naveen Chopra, and Kentaro Morimitsu, the disclosure of which is totally incorporated herein by reference.

Reference is made to U.S. Pub. No. 20140139591 entitled "Ink Compositions Incorporating Ester Resins," with the named inventors Adela Goredema, Jennifer L. Belelie, Rina Carlini, Naveen Chopra, Kentaro Morimitsu, Corey L. Tracy, and Nathan M. Bamsey, the disclosure of which is totally incorporated herein by reference.

Reference is made to U.S. Pub. No. 20130284063 entitled "Bio-renewable Fast Crystallizing Phase Change Inks," with the named inventors Adela Goredema, Jennifer Belelie, Kentaro Morimitsu, Guerino Sacripante, Gabriel Iftime, Caroline Turek, Corey Tracy and Nathan Bamsey, the disclosure of which is totally incorporated herein by reference.

Reference is made to U.S. Pat. No. 8,591,640 entitled "Bio-renewable Fast Crystallizing Phase Change Inks," with the named inventors Adela Goredema, Jennifer Belelie, Kentaro Morimitsu, Gabriel Iftime, Rina Carlini, Caroline Turek, Corey Tracy and Nathan Bamsey, the disclosure of which is totally incorporated herein by reference.

Reference is made to U.S. Pub. No. 20140137768 entitled "Bio-Renewable Phase Change Inks Comprising Recycled Resin Materials," with the named inventors Daryl W. Vanbesien, Guerino Sacripante, Adela Goredema, Naveen Chopra, and Gabriel Iftime, the disclosure of which is totally incorporated herein by reference.

BACKGROUND

Disclosed herein are oligomeric rosin ester compounds suitable for use in inks and other applications.

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing, as disclosed in, for example, U.S. Pat. No. 5,496,879 and German Patent Publications DE 4205636AL and DE 4205713AL, the disclosures of each of which are totally incorporated herein by reference.

Phase change inks are desirable for ink jet printers because they remain in a solid phase at room temperature during shipping, long term storage, or the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, or the like), the droplets solidify immediately upon contact with the substrate, so that migration of ink along the printing medium is prevented and dot quality is improved.

Known phase change inks generally contain components such as crystalline waxes and other materials that enable sharp and rapid phase transitions from the molten liquid state to the solid state. Many known phase change inks, however, exhibit disadvantages such as poor adhesion to coated paper substrates, resulting in poor scratch-resistance, poor image robustness, hard and brittle properties, poor 'paper fold' performance such as cracking and creasing of the image when the document is folded, and document offset. Further, the nonpolarity of these ink components often leads to compatibility issues with commonly available dyes and pigments, resulting in the need for more expensive or custom-designed colorants to ensure good solubility or dispersibility in the ink carrier and good long-term thermal stability to prevent colorant degradation or colorant migration.

Customers have also created a demand for materials that are bio-based, or derived at least partly from renewable resources. Energy and environmental policies, increasing and volatile oil prices, and public/political awareness of the rapid depletion of global fossil reserves has created a need to find sustainable monomers derived from biomaterials. By using bio-renewable feedstock, manufacturers can reduce their carbon footprint and move to a zero-carbon or even a carbon-neutral footprint. Bio-based polymers can also be very attractive in terms of specific energy and emission savings. Using bio-based feedstock can help provide new sources of income for domestic agriculture and reduce the economic risks and uncertainty associated with reliance on petroleum imported from unstable regions.

Accordingly, while known materials and processes are suitable for their intended purposes, there is a need for improved phase change inks. In addition, there is a need for phase change inks that exhibit sharp and rapid phase transitions from the molten liquid state to the solid state. Further, there is a need for phase change inks that exhibit good adhesion to coated paper substrates. Additionally, there is a need for phase change inks that exhibit good scratch-resistance. There is also a need for phase change inks that exhibit good image robustness. In addition, there is a need for phase change inks that exhibit good "paper fold" performance and reduced cracking and creasing of the image when the document is folded. Further, there is a need for phase change inks that exhibit good document offset performance. Additionally, there is a need for phase change inks that exhibit good compatibility with commonly available colorants. In addition, a need remains for phase change inks that contain at least some materials at least partly derived from renewable resources. Further, a need remains for phase change inks that can be prepared at desirably low cost. Additionally, a need remains for phase change inks that contain some biodegradable components.

SUMMARY

Disclosed herein is a compound: (a) of the formula

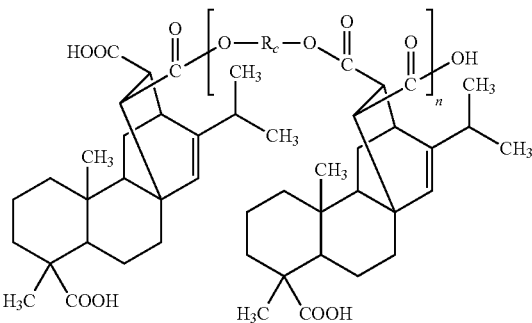

wherein $R_c$ is: (i) alkylene, including substituted unsubstituted alkylene, wherein hetero atoms either may or may not be present in alkylene; (ii) arylene, including substituted and unsubstituted arylene, wherein hetero atoms either may or may not be present in arylene; (iii) arylalkylene, including substituted and unsubstituted arylalkylene, wherein hetero atoms either may or may not be present in either or both of the alkyl portion and the aryl portion of arylalkylene; or (iv) alkylarylene, including substituted and unsubstituted alkylarylene, wherein hetero atoms either may or may not be present in either or both of the alkyl portion and the aryl portion of alkylarylene; and n is an integer representing the number of repeat monomer units; or (b) of the formula

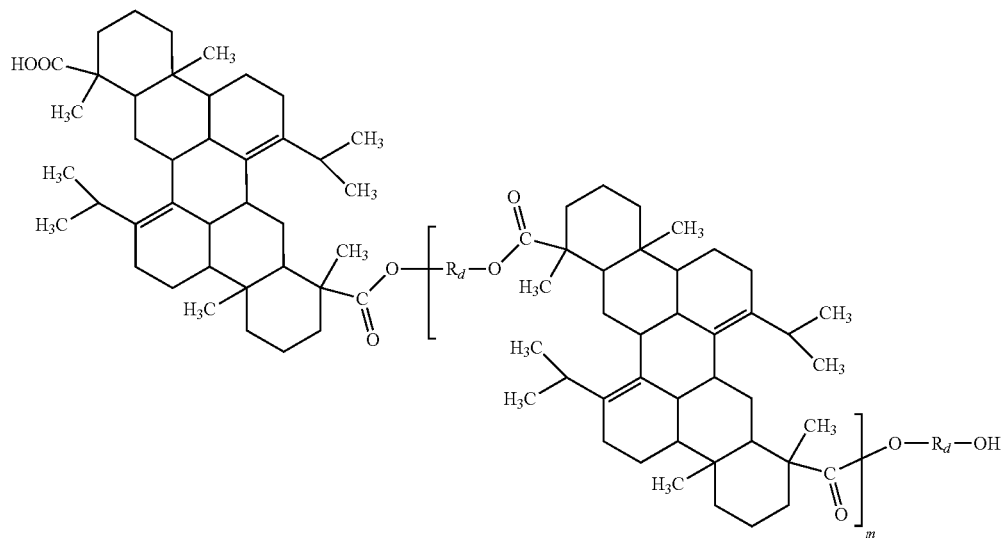

wherein $R_d$ is: (i) alkylene, including substituted unsubstituted alkylene, wherein hetero atoms either may or may not be present in alkylene; (ii) arylene, including substituted and unsubstituted arylene, wherein hetero atoms either may or may not be present in arylene; (iii) arylalkylene, including substituted and unsubstituted arylalkylene, wherein hetero atoms either may or may not be present in either or both of the alkyl portion and the aryl portion of arylalkylene; or (iv) alkylarylene, including substituted and unsubstituted alkylarylene, wherein hetero atoms either may or may not be present in either or both of the alkyl portion and the aryl portion of alkylarylene; and m is an integer representing the number of repeat monomer units.

BRIEF DESCRIPTION OF THE DRAWINGS

The FIGURE is a plot showing the rheology characteristics for oligomeric materials as disclosed herein.

DETAILED DESCRIPTION

As used herein:

Alkyl refers to a monovalent alliphatic hydrocarbon group having no aromatic moieties or substituents thereon;

Alkylene refers to a divalent or higher alliphatic hydrocarbon group having no aromatic moieties or substituents thereon;

Aryl refers to a monovalent aromatic hydrocarbon group having no aliphatic moieties or substituents thereon;

Arylene refers to a divalent or higher aromatic hydrocarbon group having no aliphatic moieties or substituents thereon;

Arylalkyl refers to a monovalent aliphatic hydrocarbon group having one or more aromatic moieties or substituents thereon, wherein the point of attachment of the group is through the aliphatic group, such as benzyl or the like;

Arylalkylene refers to a divalent or higher aliphatic hydrocarbon group having one or more aromatic moieties or substituents thereon, wherein the points of the attachment of the group are either (1) all through the aliphatic group, with an example being

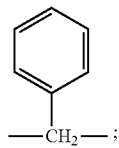

or (2) with at least one through the aliphatic group and at least one through the aromatic group, with an example being

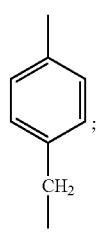

Alkylaryl refers to a monovalent aromatic hydrocarbon group having one or more aliphatic moieties or substituents thereon, wherein the point of attachment of the group is through the aromatic group, such as tolyl or the like;

Alkylarylene refers to a divalent or higher aromatic hydrocarbon group having one or more aliphatic moieties or substituents thereon, wherein the points of attachment of the group are both through the aromatic group, with an example being

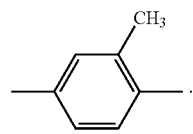

The oligomeric ester materials disclosed herein are derived from rosin. Rosin is generally derived from conifers and other plants and comprises mixtures of organic acids such as abietic acid and related compounds and isomers, including (but not limited to) neoabietic acid, palustric acid, pimaric acid, levo-pimaric acid, isopimaric acid, dehydroabietic acid, sandaracopimaric acid, and the like:

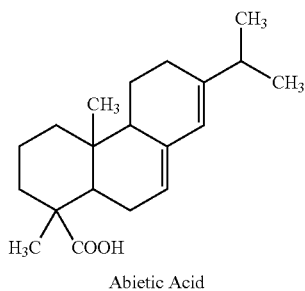

Abietic Acid

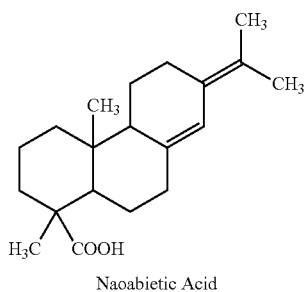

Naoabietic Acid

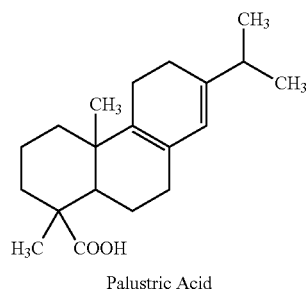

Palustric Acid

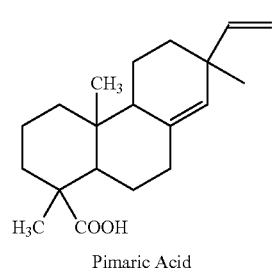

Pimaric Acid

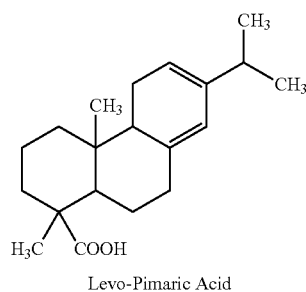

Levo-Pimaric Acid

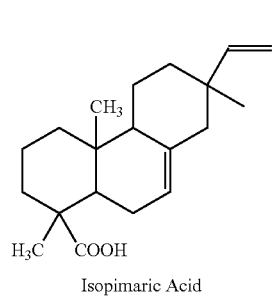

Isopimaric Acid

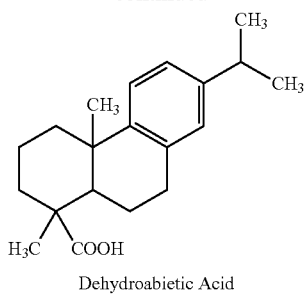

Dehydroabietic Acid

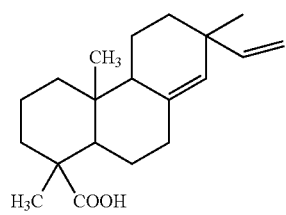

Sandaracopimarc Acid

These materials can be further reacted with acids or anhydrides to provide monomers useful for making oligoester resins. For example, abietic acid reacts with acrylic acid to generate a compound as follows:

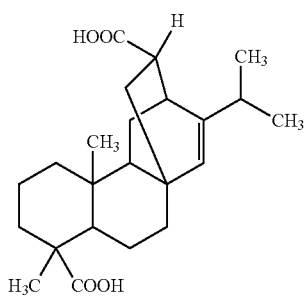

Acrylic Acid-Modified Abietic Acid with fumaric acid to generate a compound as follows:

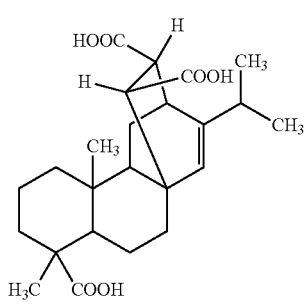

Fumaric Acid-Modified Abietic Acid and with maleic anhydride to generate a compound as follows:

Maleic Anhydride-Modified Abietic Acid

Esters can be formed from functionalized rosins. "Functionalized" means that the rosin has thereon a functional group or combination of functional groups, such as carboxylic acid groups, ester groups, anhydride groups, or the like, that can undergo a polycondensation reaction with an alcohol or diol (or higher alcohol) to form an ester or oligoester. The esters can be formed from various alcohols, such as diols, of the formula HO—$R_2$—OH, wherein $R_2$ is (1) alkylene, including linear, branched, saturated, unsaturated, cyclic, substituted, and unsubstituted alkylene, wherein hetero atoms, such as oxygen, nitrogen, sulfur, silicon, phosphorus, boron, and the like either may or may not be present in alkylene, in one embodiment with at least about 2 carbons, in another embodiment with at least about 4 carbons, and in yet another embodiment with at least about 6 carbons, and in one embodiment with no more than about 40 carbons, in another embodiment with no more than about 22 carbons, and in yet another embodiment with no more than about 12 carbons, although the number of carbons can be outside of these ranges, (2) arylene, including substituted and unsubstituted arylene, wherein hetero atoms, such as oxygen, nitrogen, sulfur, silicon, phosphorus, boron, and the like either may or may not be present in arylene, in one embodiment with at least about 6 carbons, in another embodiment with at least about 8 carbons, and in yet another embodiment with at least about 12 carbons, and in one embodiment with no more than about 40 carbons, in another embodiment with no more than about 22 carbons, and in yet another embodiment with no more than about 16 carbons, although the number of carbons can be outside of these ranges, such as phenylene or the like, (3) arylalkylene, including substituted and unsubstituted arylalkylene, wherein the alkyl portion of arylalkylene can be linear, branched, saturated, unsaturated, and/or cyclic, wherein hetero atoms, such as oxygen, nitrogen, sulfur, silicon, phosphorus, boron, and the like either may or may not be present in either or both of the alkyl portion and the aryl portion of arylalkylene, in one embodiment with at least about 7 carbons, in another embodiment with at least about 8 carbons, and in yet another embodiment with at least about 10 carbons, and in one embodiment with no more than about 40 carbons, in another embodiment with no more than about 22 carbons, and in yet another embodiment with no more than about 16 carbons, although the number of carbons can be outside of these ranges, such as benzylene or the like, or (4) alkylarylene, including substituted and unsubstituted alkylarylene, wherein the alkyl portion of alkylarylene can be linear, branched, saturated, unsaturated, and/or cyclic, wherein hetero atoms, such as oxygen, nitrogen, sulfur, silicon, phosphorus, boron, and the like either may or may not be present in either or both of the alkyl portion and the aryl portion of alkylarylene, in one embodiment with at least about 7 carbons, in another embodiment with at least about 8 carbons, and in yet another embodiment with at least about 10 carbons, and in one embodiment with no more than about 40 carbons, in another embodiment with no more than about 22 carbons, and in yet another embodiment with no more than about 16 carbons, although the number of carbons can be outside of these ranges, such as tolylene or the like; such as triethylene glycol, dipropylene glycol, ethylene glycol, diethylene glycol, other alkylene glycols such as propylene glycol, 1,3- and 1,4-butanediols, 1,6-hexanediol, 3-methyl-1,5-pentanediol, neopentyl glycol, and the like; triols, of the formula $R_3$—$(OH)_3$, wherein $R_3$ is (1) alkylene, including linear, branched, saturated, unsaturated, cyclic, substituted, and unsubstituted alkylene, wherein hetero atoms, such as oxygen, nitrogen, sulfur, silicon, phosphorus, boron, and the like either may or may not be present in alkylene, in one embodiment with at least about 1 carbon, in another embodiment with at least about 4 carbons, and in yet another embodiment with at least about 6 carbons, and in one embodiment with no more than about 40 carbons, in another embodiment with no more than about 22 carbons, and in yet another embodiment with no more than about 12 carbons, although the number of carbons can be outside of these ranges, (2) arylene, including substituted and unsubstituted arylene, wherein hetero atoms, such as oxygen, nitrogen, sulfur, silicon, phosphorus, boron, and the like either may or may not be present in arylene, in one embodiment with at least about 6 carbons, in another embodiment with at least about 8 carbons, and in yet another embodiment with at least about 12 carbons, and in one embodiment with no more than about 40 carbons, in another embodiment with no more than about 22 carbons, and in yet another embodiment with no more than about 12 carbons, although the number of carbons can be outside of these ranges, such as phenylene or the like, (3) arylalkylene, including substituted and unsubstituted arylalkylene, wherein the alkyl portion of arylalkylene can be linear, branched, saturated, unsaturated, and/or cyclic, wherein hetero atoms, such as oxygen, nitrogen, sulfur, silicon, phosphorus, boron, and the like either may or may not be present in either or both of the alkyl portion and the aryl portion of arylalkylene, in one embodiment with at least about 7 carbons, in another embodiment with at least about 8 carbons, and in yet another embodiment with at least about 10 carbons, and in one embodiment with no more than about 40 carbons, in another embodiment with no more than about 22 carbons, and in yet another embodiment with no more than about 16 carbons, although the number of carbons can be outside of these ranges, such as benzylene or the like, or (4) alkylarylene, including substituted and unsubstituted alkylarylene, wherein the alkyl portion of alkylarylene can be linear, branched, saturated, unsaturated, and/or cyclic, wherein hetero atoms, such as oxygen, nitrogen, sulfur, silicon, phosphorus, boron, and the like either may or may not be present in either or both of the alkyl portion and the aryl portion of alkylarylene, in one embodiment with at least about 7 carbons, in another embodiment with at least about 8 carbons, and in yet another embodiment with at least about 12 carbons, and in one embodiment with no more than about 40 carbons, in another embodiment with no more than about 22 carbons, and in yet another embodiment with no more than about 16 carbons, although the number of carbons can be outside of these ranges, such as tolylene or the like; such as glycerol, trimethylolpropane, trimethylolethane, hexane triols, and the like; tetrols, of the formula $R_4$—$(OH)_4$, wherein $R_4$ is (1) alkylene, including linear, branched, saturated, unsaturated, cyclic, substituted, and unsubstituted alkylene, wherein hetero atoms, such as oxygen, nitrogen, sulfur, silicon, phosphorus, boron, and the like either may or may not be present in alkylene, in one embodiment with at least about 1 carbon, in another embodiment with at least about 4 carbons, and in yet another embodiment with at least about 6 carbons, and in one embodiment with no more than about 40 carbons, in another embodiment with no more than about 22 carbons, and in yet another embodiment with no more than about 12 carbons, although the number of carbons can be outside of these ranges, (2) arylene, including substituted and unsubstituted arylene, wherein hetero atoms, such as oxygen, nitrogen, sulfur, silicon, phosphorus, boron, and the like either may or may not be present in arylene, in one embodiment with at least about 6 carbons, in another embodiment with at least about 8 carbons, and in yet another embodiment with at least about 12 carbons, and in one embodiment with no more than about 40 carbons, in another embodiment with no more than about 22 carbons, and in yet another embodiment with no more than about 12 carbons, although the number of carbons can be outside of these ranges, such as phenylene or the like, (3) arylalkylene, including substituted and unsubstituted arylalkylene, wherein the alkyl portion of arylalkylene can be linear, branched, saturated, unsaturated, and/or cyclic, wherein hetero atoms, such as oxygen, nitrogen, sulfur, silicon, phosphorus, boron, and the like either may or may not be present in either or both of the alkyl portion and the aryl portion of arylalkylene, in one embodiment with at least about 7 carbons, in another embodiment with at least about 8 carbons, and in yet another embodiment with at least about 10 carbons, and in one embodiment with no more than about 40 carbons, in another embodiment with no more than about 22 carbons, and in yet another embodiment with no more than about 16 carbons, although the number of carbons can be outside of these ranges, such as benzylene or the like, or (4) alkylarylene, including substituted and unsubstituted alkylarylene, wherein the alkyl portion of alkylarylene can be linear, branched, saturated, unsaturated, and/or cyclic, wherein hetero atoms, such as oxygen, nitrogen, sulfur, silicon, phosphorus, boron, and the like either may or may not be present in either or both of the alkyl portion and the aryl portion of alkylarylene, in one embodiment with at least about 7 carbons, in another embodiment with at least about 8 carbons, and in yet another embodiment with at least about 12 carbons, and in one embodiment with no more than about 40 carbons, in another embodiment with no more than about 22 carbons, and in yet another embodiment with no more than about 16 carbons, although the number of carbons can be outside of these ranges, such as tolylene or the like; such as pentaerythritol, alpha-methylglucoside, diglycerol, and the like, wherein the substituents on the substituted alkyl, alkylene, aryl, arylene, arylalkyl, arylalkylene, alkylaryl, and alkylarylene groups can be (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, silyl groups, siloxyl groups, silane groups, mixtures thereof, and the like, wherein two or more substituents can be joined together to form a ring.

Further, rosins can be dimerized to provide materials having two or more carboxylic acid groups thereon. Dimerized rosins are also often referred to in the art as polymerized rosins, although "polymerized rosin" also typically refers to the resinous mixture comprising unrefined reaction products containing non-dimerizable rosin acids such as dehydroabietic acid, rosin acids containing some unsaturation which do not react, a number of different types of polymerized rosin acids including dimerized rosin acids, esters, rosin acid anhydrides, and non-saponifiable substances. Dimerized or polymerized rosins can be made as described in, for example, U.S. Pat. Nos. 2,017,866, 2,108,928, 2,136,525, 2,307,641, 2,322,316, 2,328,681, 2,375,618, 2,492,146, 2,515,218, 4,414,146, and 4,536,333, and in Parkin, Jr. et al., "Thermal Dimerization of Rosin," *Ind. Eng. Chem. Prod. Res. Dev.*, 8(3), pp. 304-306 (1969), Sinclair et al., "Influence of Reaction Conditions on the Dimerization of Abietic Acid and Rosin," *Ind. Eng. Chem. Prod. Res. Dev.*, 9(1), pp. 60-65 (1970), and Fujii et al., "Dimeric Components from the Dimerization of Abietic Acid," *JAOCS*, 64(8), pp. 1144-1149 (1987), the disclosures of each of which are totally incorporated herein by reference. Dimerized rosin is believed to have a number of different structures, as in, for example, the following compound

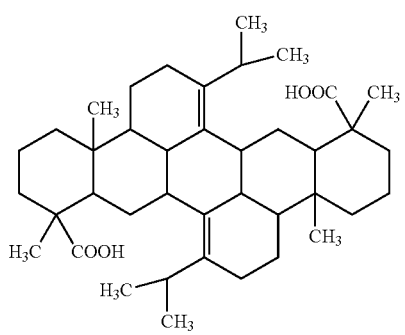

Dimerized Rosin available as DYMEREX from Eastman Chemical Co., as well as the following other proposed structures:

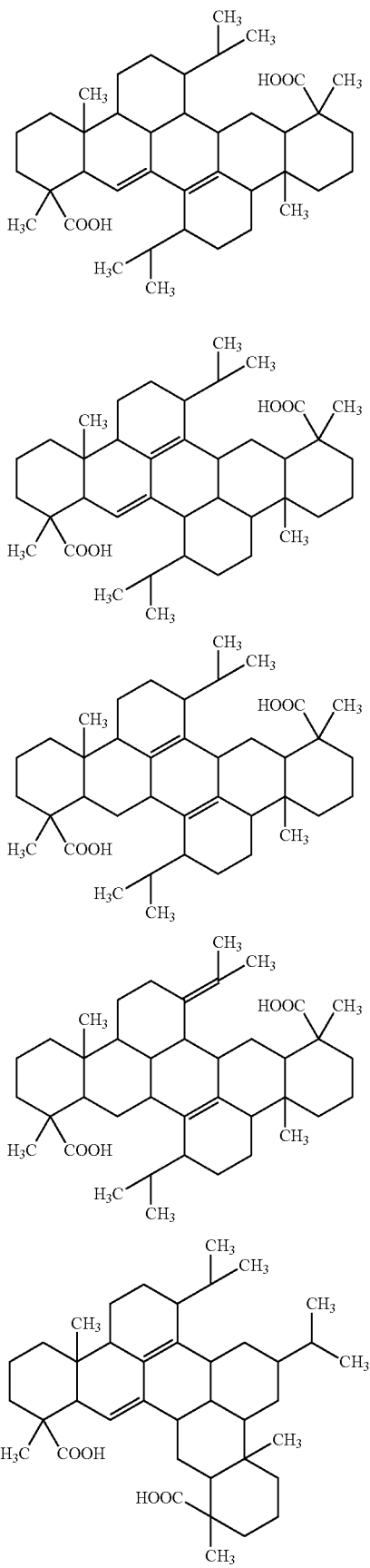

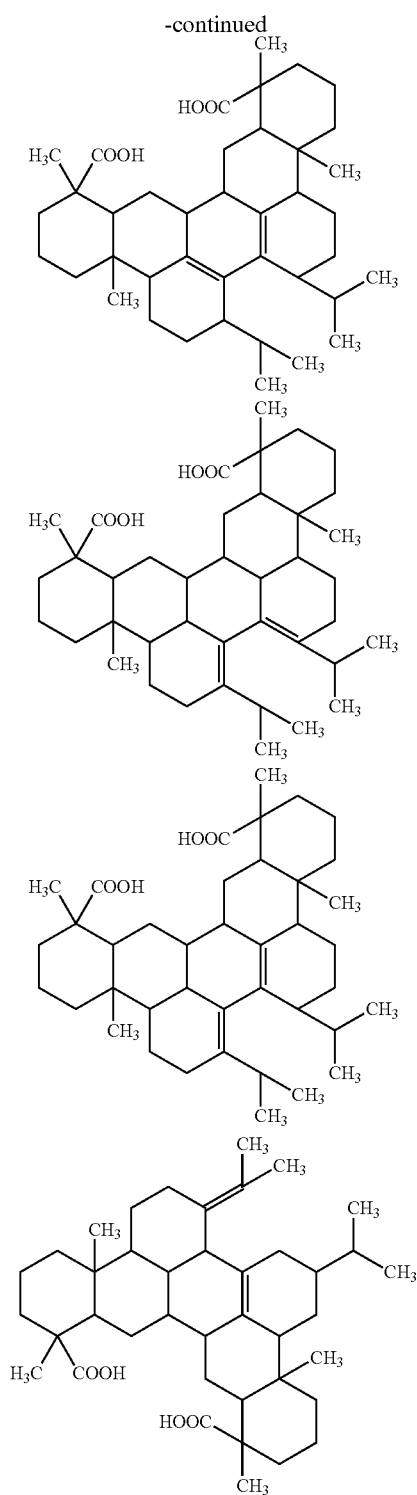

and the like, and all dimerized rosins are suitable for the purposes of the present disclosure.

The reaction conditions between rosin acids and the acids and anhydrides are known in the art and are described in, for example, "Preparation of Acrylic Modified Rosin," Noah J. Halbrook and Ray V. Lawrence, *Ind. Eng. Chem. Prod. Res. Develop.*, Vol. 11, No. 2, p. 200-202, 1972, "Fumaric Modified Resin," Noah J. Halbrook and Ray V. Lawrence, *Industrial and Engineering Chemistry*, Vol. 50, No. 3, March 1958, pp. 321-322, and "Rosin-based acid anhydrides as alternatives to petrochemical curing agents," Xiaoqing Liu, Wenbo Xin, and Jinwen Zhang, *Green Chem.*, 2009, 11, 1018-1025, the disclosures of each of which are totally incorporated herein by reference.

In one specific embodiment, the rosin is reacted with diol or higher alcohol (hereinafter collectively referred to as "alcohols") specifically selected to be bio-renewable. Examples of bio-renewable alcohols include (but are not limited to) 1,4-butanediol, 1,3-propanediol, cyclohexanedimethanol, of the formula

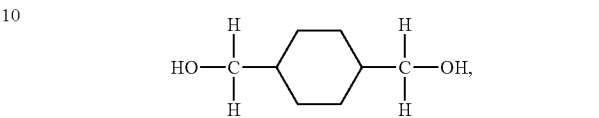

or the like, as well as mixtures thereof.

When a rosin derivative having two or more acid functional groups is reacted with a diol, triol, tetrol, or higher alcohol, oligomers (having, in one specific embodiment, from about 1 to about 10 repeat monomer units) can be formed. Examples of oligomers include those formed from the reaction of a rosin having three or more acid functional groups with a diol, such as fumaric acid-modified rosin with a diol, as follows:

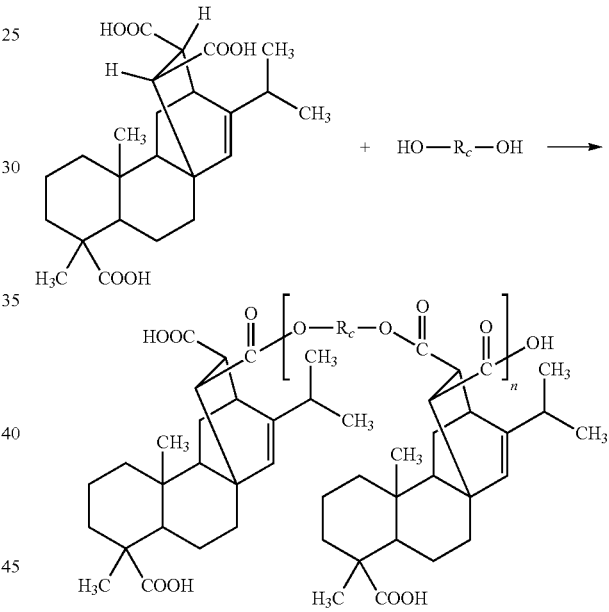

wherein $R_c$ is:

(i) alkylene, including linear, branched, saturated, unsaturated, cyclic, substituted, and unsubstituted alkylene, wherein hetero atoms, such as oxygen, nitrogen, sulfur, silicon, phosphorus, boron, and the like either may or may not be present in alkylene, in one embodiment with at least about 2 carbons, in another embodiment with at least about 4 carbons, and in yet another embodiment with at least about 6 carbons, and in one embodiment with no more than about 40 carbons, in another embodiment with no more than about 22 carbons, and in yet another embodiment with no more than about 12 carbons, although the number of carbons can be outside of these ranges;

(ii) arylene, including substituted and unsubstituted arylene, wherein hetero atoms, such as oxygen, nitrogen, sulfur, silicon, phosphorus, boron, and the like either may or may not be present in arylene, in one embodiment with at least about 6 carbons, in another embodiment with at least about 8 carbons, and in yet another embodiment with at least about 12 carbons, and in one embodiment with no more than about 40 carbons, in another embodiment with no more than about 22 carbons, and in yet another embodiment with no more than about 16 carbons, although the number of carbons can be outside of these ranges, such as phenylene or the like;

(iii) arylalkylene, including substituted and unsubstituted arylalkylene, wherein the alkyl portion of arylalkylene can be linear, branched, saturated, unsaturated, and/or cyclic, wherein hetero atoms, such as oxygen, nitrogen, sulfur, silicon, phosphorus, boron, and the like either may or may not be present in either or both of the alkyl portion and the aryl portion of arylalkylene, in one embodiment with at least about 7 carbons, in another embodiment with at least about 8 carbons, and in yet another embodiment with at least about 10 carbons, and in one embodiment with no more than about 40 carbons, in another embodiment with no more than about 22 carbons, and in yet another embodiment with no more than about 16 carbons, although the number of carbons can be outside of these ranges, such as benzylene or the like; or (iv) alkylarylene, including substituted and unsubstituted alkylarylene, wherein the alkyl portion of alkylarylene can be linear, branched, saturated, unsaturated, and/or cyclic, wherein hetero atoms, such as oxygen, nitrogen, sulfur, silicon, phosphorus, boron, and the like either may or may not be present in either or both of the alkyl portion and the aryl portion of alkylarylene, in one embodiment with at least about 7 carbons, in another embodiment with at least about 8 carbons, and in yet another embodiment with at least about 10 carbons, and in one embodiment with no more than about 40 carbons, in another embodiment with no more than about 22 carbons, and in yet another embodiment with no more than about 16 carbons, although the number of carbons can be outside of these ranges, such as tolylene or the like; wherein the substituents on the substituted alkylene, arylene, arylalkylene, and alkylarylene groups can be (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, silyl groups, siloxyl groups, silane groups, mixtures thereof, and the like, wherein two or more substituents can be joined together to form a ring, and n is an integer representing the number of repeat monomer units, being in one embodiment at least about 1, and in another embodiment at least about 2, and in one embodiment no more than about 10, although the number can be outside of these ranges.

Specific examples of these oligoesters include (but are not limited to) oligoesters of fumaric acid-modified rosin with 1,4-butanediol, wherein $R_c$ is —$(CH_2)_4$—, oligoesters of fumaric acid-modified resin with 1,4-cyclohexanedimethanol, wherein $R_c$ is

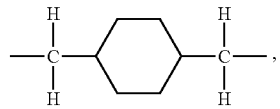

and the like, as well as mixtures thereof.

Additional examples include those formed from dimerized rosins, such as dimerized abietic acid, having two acid groups, with a diol, as follows:

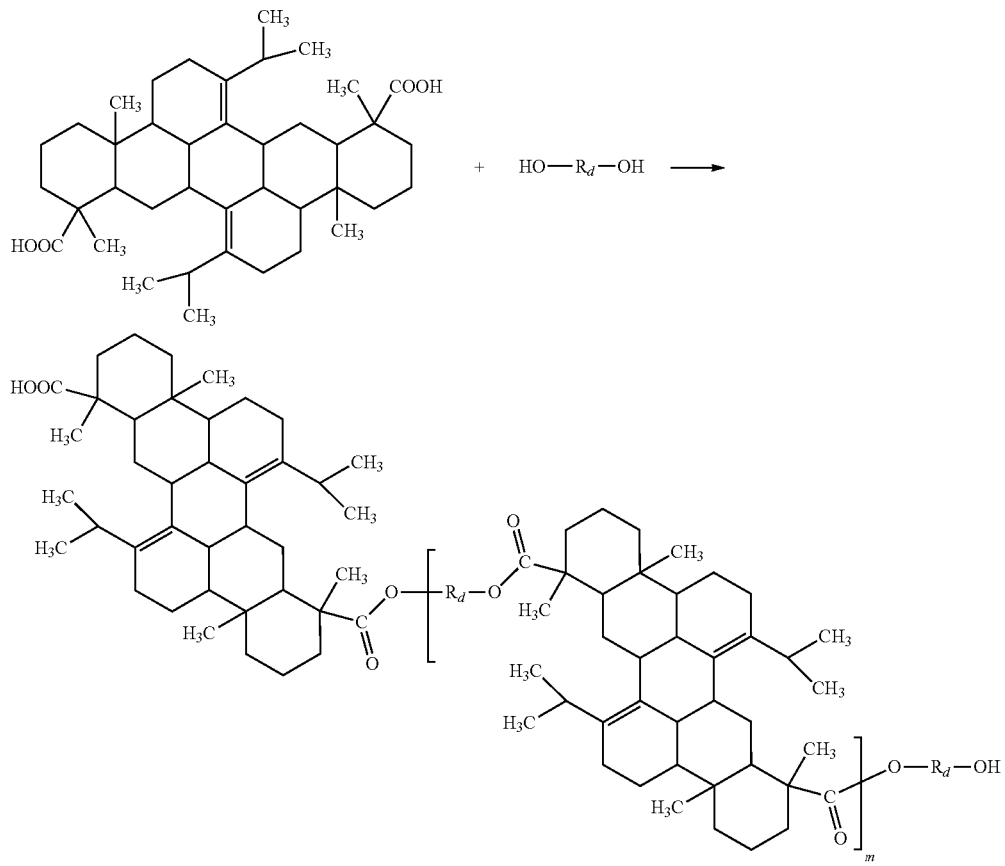

wherein $R_d$ is:

(i) alkylene, including linear, branched, saturated, unsaturated, cyclic, substituted, and unsubstituted alkylene, wherein hetero atoms, such as oxygen, nitrogen, sulfur, silicon, phosphorus, boron, and the like either may or may not be present in alkylene, in one embodiment with at least about 2 carbons, in another embodiment with at least about 4 carbons, and in yet another embodiment with at least about 6 carbons, and in one embodiment with no more than about 40 carbons, in another embodiment with no more than about 22 carbons, and in yet another embodiment with no more than about 12 carbons, although the number of carbons can be outside of these ranges;

(ii) arylene, including substituted and unsubstituted arylene, wherein hetero atoms, such as oxygen, nitrogen, sulfur, silicon, phosphorus, boron, and the like either may or may not be present in arylene, in one embodiment with at least about 6 carbons, in another embodiment with at least about 8 carbons, and in yet another embodiment with at least about 12 carbons, and in one embodiment with no more than about 40 carbons, in another embodiment with no more than about 22 carbons, and in yet another embodiment with no more than about 16 carbons, although the number of carbons can be outside of these ranges, such as phenylene or the like;

(iii) arylalkylene, including substituted and unsubstituted arylalkylene, wherein the alkyl portion of arylalkylene can be linear, branched, saturated, unsaturated, and/or cyclic, wherein hetero atoms, such as oxygen, nitrogen, sulfur, silicon, phosphorus, boron, and the like either may or may not be present in either or both of the alkyl portion and the aryl portion of arylalkylene, in one embodiment with at least about 7 carbons, in another embodiment with at least about 8 carbons, and in yet another embodiment with at least about 10 carbons, and in one embodiment with no more than about 40 carbons, in another embodiment with no more than about 22 carbons, and in yet another embodiment with no more than about 16 carbons, although the number of carbons can be outside of these ranges, such as benzylene or the like; or (iv) alkylarylene, including substituted and unsubstituted alkylarylene, wherein the alkyl portion of alkylarylene can be linear, branched, saturated, unsaturated, and/or cyclic, wherein hetero atoms, such as oxygen, nitrogen, sulfur, silicon, phosphorus, boron, and the like either may or may not be present in either or both of the alkyl portion and the aryl portion of alkylarylene, in one embodiment with at least about 7 carbons, in another embodiment with at least about 8 carbons, and in yet another embodiment with at least about 10 carbons, and in one embodiment with no more than about 40 carbons, in another embodiment with no more than about 22 carbons, and in yet another embodiment with no more than about 16 carbons, although the number of carbons can be outside of these ranges, such as tolylene or the like; wherein the substituents on the substituted alkylene, arylene, arylalkylene, and alkylarylene groups can be (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, silyl groups, siloxyl groups, silane groups, mixtures thereof, and the like, wherein two or more substituents can be joined together to form a ring, and m is an integer representing the number of repeat monomer units, being in one embodiment at least about 1, and in another embodiment at least about 2, and in one embodiment no more than about 10, although the number can be outside of these ranges.

For example, when the diol is 1,4-cyclohexanedimethanol, $R_d$ is

The oligoesters disclosed herein have weight average molecular weights (Mw) of in one embodiment at least about 600 g/mol, and in another embodiment at least about 800 g/mol, and in one embodiment no more than about 10,000 g/mol, and in another embodiment no more than about 2,000 g/mol, although the values can be outside of these ranges.

The oligoesters disclosed herein have polydispersity values of in one embodiment at least about 1, and in one embodiment no more than about 2, although the values can be outside of these ranges.

The compounds disclosed herein have glass transition temperatures (midpoint Tg) of in one embodiment at least about 1° C., and in another embodiment at least about 5° C., and in one embodiment no more than about 30° C., and in another embodiment no more than about 25° C., although the values can be outside of these ranges.

The glass transition temperatures of the materials disclosed herein can be determined by differential scanning calorimetry (DSC), with, for example, a TA Instruments Q100 apparatus, using a heating and cooling temperature gradient of 10° C. per minute and measuring the Tg after a second repeat cycle of heating and cooling (to remove thermal history of the sample).

Biorenewable content (% BRC) is defined as the weight percent of biorenewable portion of the material with respect to the total mass of the material in a composition. The materials disclosed herein have a % BRC of in one embodiment at least about 60%, in another embodiment at least about 70%, and in yet another embodiment at least about 80%, although the value can be outside of these ranges.

The materials disclosed herein are suitable for use in applications such as ink compositions, including as binders in printing inks such as ink jet inks, offset litho inks, flexo inks, gravure inks, or the like. They can also find use in applications such as adhesives and tackifier materials.

Specific embodiments will now be described in detail. These examples are intended to be illustrative, and the claims are not limited to the materials, conditions, or process parameters set forth in these embodiments. All parts and percentages are by weight unless otherwise indicated.

Example I

Synthesis of Fumaric Acid-Modified Rosin/Butanediol Oligoester A

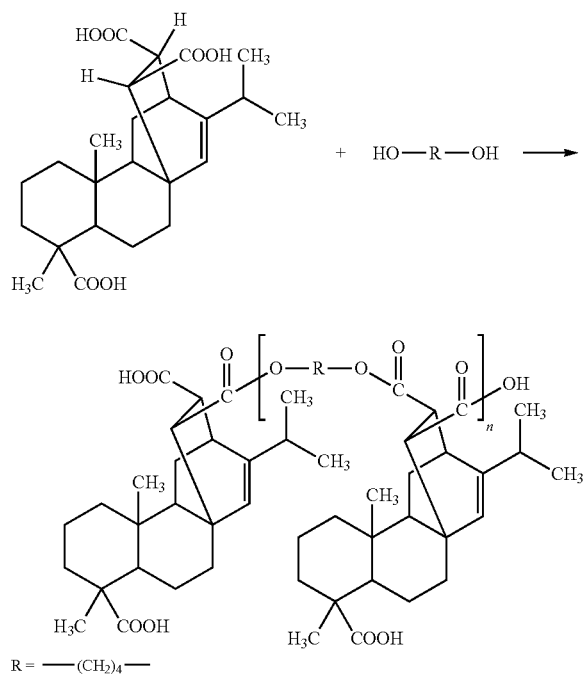

In a 200 mL round-bottom flask equipped with a water condenser was charged fumaric-modified rosin acid (obtained from HARIMA; 10.0 g, 24 mmol), 1,4-butanediol (1.44 g, 15.95 mmol; obtained from Aldrich), para-toluenesulfonic acid as catalyst (0.028 g, 0.160 mmol), and toluene as solvent (30 mL). The light amber solution that resulted was stirred magnetically and gradually heated to reflux temperature (internal temperature 115° C.) under argon atmosphere for a total of 10 h. Initially, the reaction mixture became quite viscous and gelled slightly in the solvent (attributed to self-association of the carboxylic acid groups in a hydrocarbon solvent), but as conversion to the oligoester proceeded, the viscosity of the solution diminished greatly and the color darkened. After the reaction was complete, the solvent was removed in vacuo, after which the mixture was diluted with more toluene (150 mL) and washed with 3×150 mL portions of deionized water and 1×50 mL portion of brine solution (saturated NaCl in water). The organic layer was dried with anhydrous $Na_2SO_4$ crystals and then filtered and concentrated under vacuum to give 10.50 g of a light amber semi-solid tacky material. MALDI-mass spectral analysis of this resin revealed molecular weight data of Mn=837, Mw=884, and polydispersity index PDI of 1.06. The average molecular weight was 890, Tg as measured by DSC was 17.2° C., the viscosity at 130° C. was 2440 centipoise, and the % BRC (amount of biorenewable content in the composition) was 100.

Example II

Synthesis of Fumaric Acid-Modified Rosin/Butanediol Oligoester B

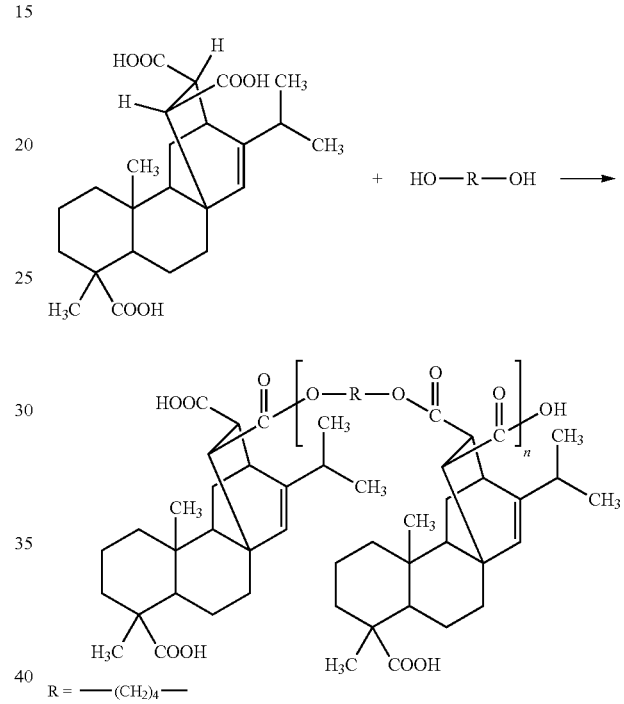

In a 200 mL round-bottom flask equipped with a water condenser was charged fumaric-modified rosin acid (obtained from HARIMA; 10.0 g, 24 mmol), 1,4-butanediol (1.56 g, 17.31 mmol; obtained from Aldrich), para-toluenesulfonic acid as catalyst (0.028 g, 0.160 mmol), and toluene as solvent (50 mL). The light amber solution that resulted was stirred magnetically and gradually heated to reflux temperature (internal temperature 115° C.) under argon atmosphere for a total of 8 h. Initially, the reaction mixture became quite viscous and gelled slightly in the solvent, but as conversion to the oligoester proceeded, the viscosity of the solution diminished greatly and the color darkened. After the reaction was complete, the solvent was removed in vacuo, after which the mixture was diluted with more toluene (200 mL) and washed with 1×50 mL portion of deionized water and 1×50 mL portion of brine solution. The organic layer was dried with anhydrous $Na_2SO_4$ crystals and then filtered and concentrated under vacuum to give 8.67 g of a light amber semi-solid tacky material. The viscosity at 130° C. was 1834 centipoise, the viscosity at 70° C. was $9.4 \times 10^7$ centipoise, and the % BRC (amount of biorenewable content in the composition) was 100.

Example III

Synthesis of Dimerized Rosin/Cyclohexanedimethanol Oligoester

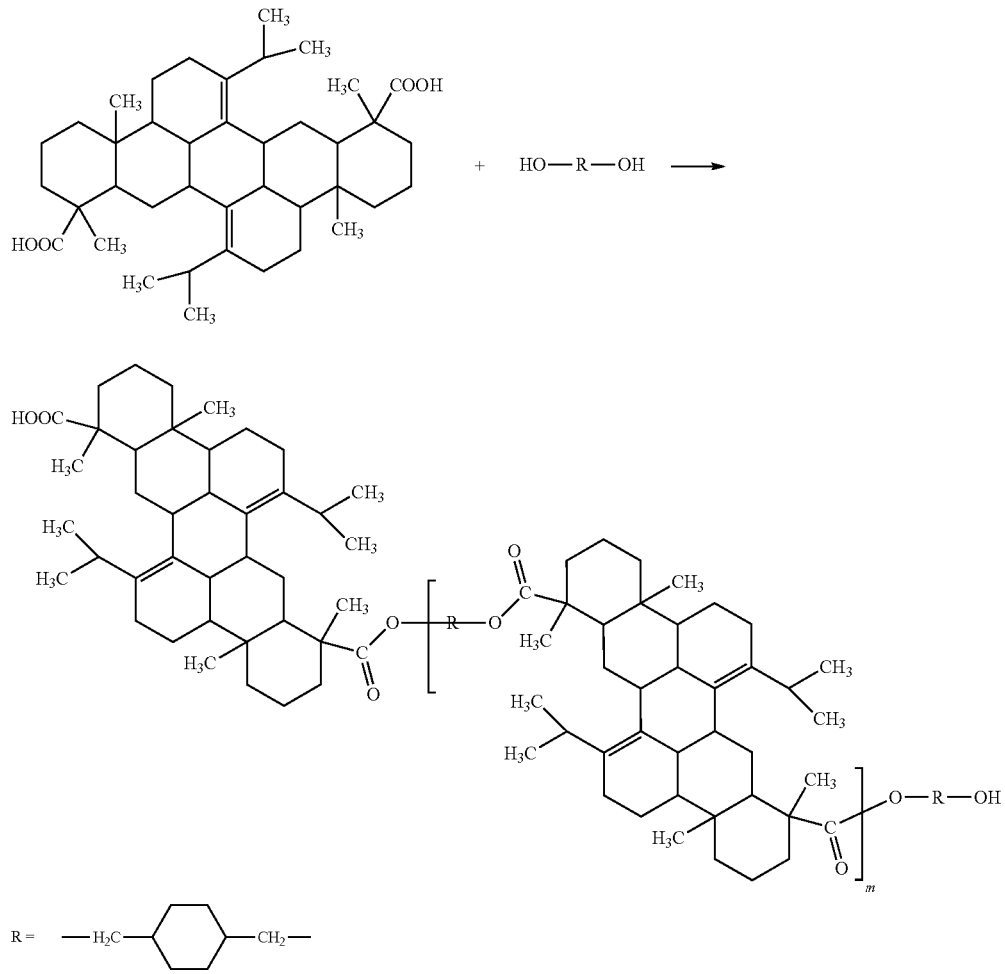

In a 200 mL round-bottom flask equipped with a water condenser was charged DYMEREX (5.00 g, 8.27 mmol; dimerized abietic acid, obtained from Eastman), 1,4-cyclohexanedimethanol (2.147 g, 14.9 mmol; obtained from Aldrich), para-toluenesulfonic acid as catalyst (0.014 g, 0.083 mmol), and toluene solvent (30 mL). The light amber solution that resulted was stirred magnetically and gradually heated to reflux temperature (internal temperature 115° C.) under argon atmosphere for a total of 10 h. As reaction conversion to the oligoester proceeded, the viscosity of the solution increased and color darkened. After the reaction was complete, the solvent was removed in vacuo, after which the mixture diluted with more toluene (150 mL) and washed with 3×150 mL portions of deionized water and 1×50 mL portion of brine solution. The organic layer was dried with anhydrous $Na_2SO_4$ crystals and then filtered and concentrated under vacuum to give 6.27 g of a tan solid material. Tg as measured by DSC was 15.3° C., the viscosity at 140° C. was 3660 centipoise, the viscosity at 70° C. was >1×10$^7$ centipoise, and the % BRC (amount of biorenewable content in the composition) was 100.

Oligomer Rheology

The oligomers prepared in Examples I through III exhibited the rheological profiles (complex viscosity versus temperature, measured at constant oscillating frequency of 1 Hz) shown in the FIGURE. The measurements were made on a strain-controlled ARES G2 rheometer (obtained from TA Instruments) using 25 mm parallel plate geometry and constant applied strain=50%.

Example IV

The process of Example I is repeated except that the 1,4-butanediol is replaced with an equimolar amount of 1,4-cyclohexanedimethanol. It is believed that similar results will be observed.

Example V

The process of Example I is repeated except that the 1,4-butanediol is replaced with an equimolar amount of propylene glycol. It is believed that similar results will be observed.

Example VI

The process of Example I is repeated except that the 1,4-butanediol is replaced with an equimolar amount of 1,3-butanediol. It is believed that similar results will be observed.

Example VII

The process of Example I is repeated except that the 1,4-butanediol is replaced with an equimolar amount of 1,6-hexanediol. It is believed that similar results will be observed.

Example VIII

The process of Example I is repeated except that the 1,4-butanediol is replaced with an equimolar amount of 3-methyl-1,5-pentanediol. It is believed that similar results will be observed.

Example IX

The process of Example I is repeated except that the 1,4-butanediol is replaced with an equimolar amount of neopentyl glycol. It is believed that similar results will be observed.

Example X

The process of Example I is repeated except that the 1,4-butanediol is replaced with an equimolar amount of 1,12-dodecanediol It is believed that similar results will be observed.

Example XI

The process of Example I is repeated except that the 1,4-butanediol is replaced with an equimolar amount of 2-methylene-1,3-propanediol It is believed that similar results will be observed.

Example XII

The process of Example I is repeated except that the 1,4-butanediol is replaced with an equimolar amount of 3-phenoxy-1,2-propanediol (Sigma-Aldrich). It is believed that similar results will be observed.

Example XIII

The process of Example III is repeated except that the 1,4-cyclohexanedimethanol is replaced with an equimolar amount of 1,4-butanediol. It is believed that similar results will be observed.

Example XIV

The process of Example III is repeated except that the 1,4-cyclohexanedimethanol is replaced with an equimolar amount of propylene glycol. It is believed that similar results will be observed.

Example XV

The process of Example III is repeated except that the 1,4-cyclohexanedimethanol is replaced with an equimolar amount of 1,3-butanediol. It is believed that similar results will be observed.

Example XVI

The process of Example III is repeated except that the 1,4-cyclohexanedimethanol is replaced with an equimolar amount of 1,6-hexanediol. It is believed that similar results will be observed.

Example XVII

The process of Example III is repeated except that the 1,4-cyclohexanedimethanol is replaced with an equimolar amount of neopentyl glycol. It is believed that similar results will be observed.

Example XVIII

The process of Example III is repeated except that the 1,4-cyclohexanedimethanol is replaced with an equimolar amount of 1,12-dodecanediol. It is believed that similar results will be observed.

Example XIX

The process of Example III is repeated except that the 1,4-cyclohexanedimethanol is replaced with an equimolar amount of 2-methylene-1,3-propanediol. It is believed that similar results will be observed.

Example XX

The process of Example III is repeated except that the 1,4-cyclohexanedimethanol is replaced with an equimolar amount of 3-phenoxy-1,2-propanediol. It is believed that similar results will be observed.

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. A compound of the formula

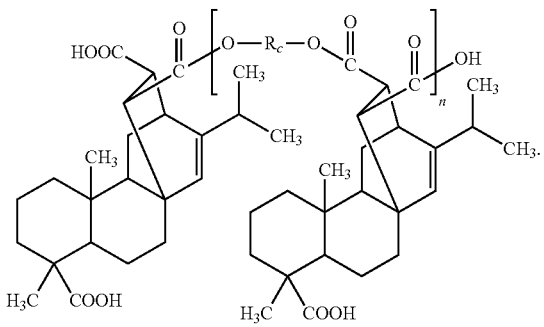

wherein $R_c$ is:
(i) alkylene, including substituted and unsubstituted alkylene, wherein hetero atoms either may or may not be present in alkylene;

(ii) arylene, including substituted and unsubstituted arylene, wherein hetero atoms either may or may not be present in arylene;
(iii) arylalkylene, including substituted and unsubstituted arylalkylene, wherein hetero atoms either may or may not be present in either or both of the alkyl portion and the aryl portion of arylalkylene; or
(iv) alkylarylene, including substituted and unsubstituted alkylarylene, wherein hetero atoms either may or may not be present in either or both of the alkyl portion and the aryl portion of alkylarylene; and n is an integer representing the number of repeat monomer units and is at least 2.

2. A compound according to claim 1 wherein R is —(CH$_2$)$_4$—.

3. A compound according to claim 1 wherein R$_c$ is

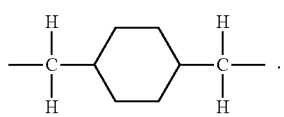

4. A compound according to claim 1 having a % BRC of at least about 80%.

5. A compound according to claim 1 wherein n is from about 2 to about 10.

6. A compound according to claim 1 wherein n is no more than about 10.

7. A compound according to claim 1 having a weight average molecular weight of from about 600 to about 10,000 g/mol.

8. A compound according to claim 1 having a % BRC of at least about 60%.

9. A compound according to claim 1 having a polydispersity of from about 1 to about 2.

10. A compound according to claim 1 having a Tg of from about 1° C. to about 30° C.

11. A compound of the formula

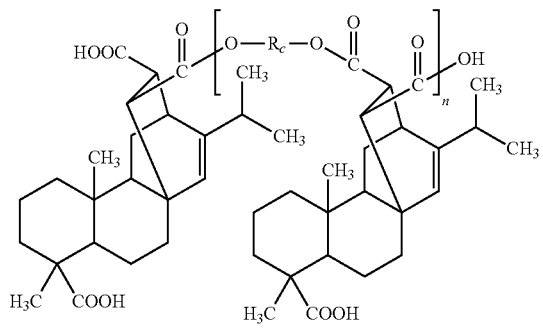

wherein R$_c$ is:
(i) alkylene having from about 2 to about 40 carbons, including substituted and unsubstituted alkylene, wherein hetero atoms either may or may not be present in alkylene;
(ii) arylene having from about 6 to about 40 carbons, including substituted and unsubstituted arylene, wherein hetero atoms either may or may not be present in arylene;
(iii) arylalkylene having from about 7 to about 40 carbons, including substituted and unsubstituted arylalkylene, wherein hetero atoms either may or may not be present in either or both of the alkyl portion and the aryl portion of arylalkylene; or
(iv) alkylarylene having from about 7 to about 40 carbons, including substituted and unsubstituted alkylarylene, wherein hetero atoms either may or may not be present in either or both of the alkyl portion and the aryl portion of alkylarylene; and n is an integer representing the number of repeat monomer units and is from about 2 to about 10.

12. A compound according to claim 11 having a weight average molecular weight of from about 600 to about 10,000 g/mol and a Tg of from about 1° C. to about 30° C.

13. A compound of the formula

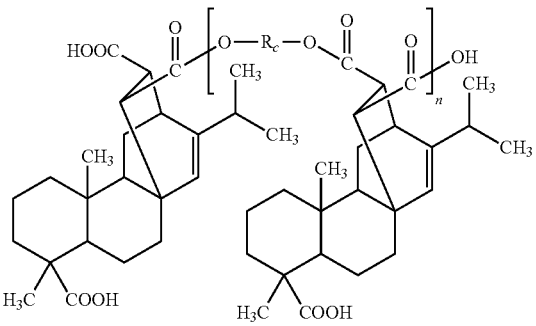

wherein R$_c$ is:
(i) alkylene having from about 4 to about 12 carbons, including substituted and unsubstituted alkylene, wherein hetero atoms either may or may not be present in alkylene;
(ii) arylene having from about 6 to about 16 carbons, including substituted and unsubstituted arylene, wherein hetero atoms either may or may not be present in arylene;
(iii) arylalkylene having from about 7 to about 16 carbons, including substituted and unsubstituted arylalkylene, wherein hetero atoms either may or may not be present in either or both of the alkyl portion and the aryl portion of arylalkylene; or
(iv) alkylarylene having from about 7 to about 16 carbons, including substituted and unsubstituted alkylarylene, wherein hetero atoms either may or may not be present in either or both of the alkyl portion and the aryl portion of alkylarylene; and n is an integer representing the number of repeat monomer units and is from about 2 to about 10.

* * * * *